United States Patent [19]

Martin

[11] Patent Number: 5,324,274
[45] Date of Patent: Jun. 28, 1994

[54] CATHETER HAVING ROTARY VALVES

[75] Inventor: Geoffrey Martin, Mississauga, Canada

[73] Assignee: Med-Pro Design, Inc., Mississauga, Canada

[21] Appl. No.: 860,389

[22] Filed: Mar. 30, 1992

[51] Int. Cl.⁵ .............................................. A61M 5/00
[52] U.S. Cl. .................................... 604/248; 137/505; 251/304; 604/29
[58] Field of Search ............... 604/248, 89, 32, 43, 604/905, 280–284, 93, 96, 29; 137/505; 251/304, 309

[56] References Cited

U.S. PATENT DOCUMENTS

| 3,411,534 | 11/1968 | Rose | 604/32 |
| 3,434,691 | 3/1969 | Hamilton | 604/248 |
| 4,079,737 | 3/1978 | Miller | 604/248 |
| 4,576,199 | 3/1986 | Svensson et al. | 604/248 |
| 4,595,005 | 6/1986 | Jinotti | 604/32 |
| 4,648,868 | 3/1987 | Hardwick et al. | 604/32 |
| 4,789,000 | 12/1988 | Aslanian | 604/248 |
| 5,053,003 | 10/1991 | Dadson et al. | 604/29 |
| 5,197,951 | 3/1993 | Mahurkar | 604/93 |

FOREIGN PATENT DOCUMENTS 0545218 2/1932 Fed. Rep. of Germany ........ 604/32

Primary Examiner—C. Fred Rosenbaum
Assistant Examiner—Chalin Smith
Attorney, Agent, or Firm—Rogers & Scott

[57] ABSTRACT

The invention provides a dual lumen vascular access catheter having a main body defining first and second lumens and a connection structure which includes coupling means attaching the structure to the main body. First and second channels extend from the respective first and second lumens for attaching the catheter to equipment, and first and second rotary valves are positioned in the respective first and second channels. The valves include operators rotatable in generally the same plane to operate the valves and to provide a ready visual indication of the positions of the valves.

7 Claims, 3 Drawing Sheets

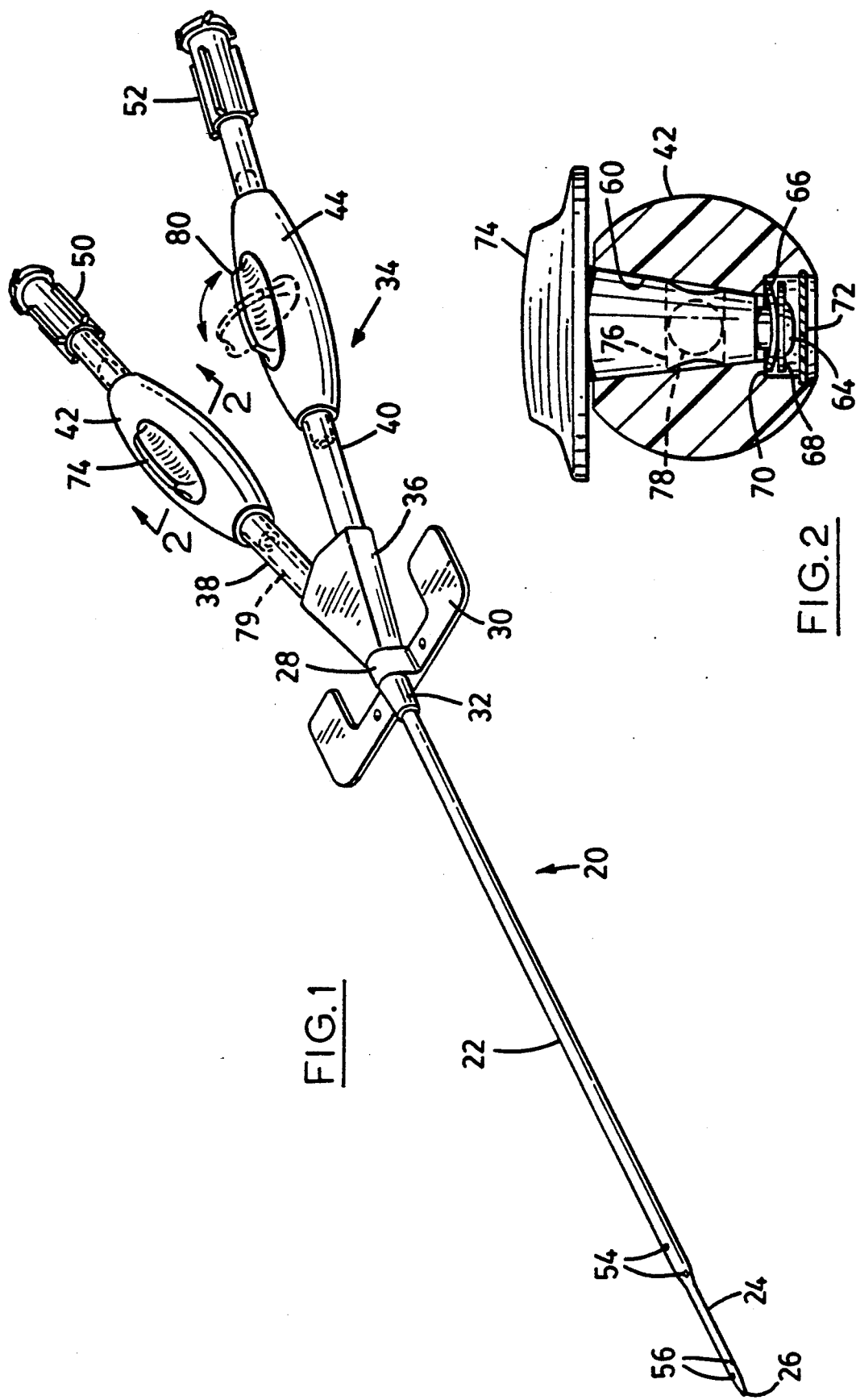

CATHETER HAVING ROTARY VALVES

This invention relates to catheters used in procedures requiring intrusion into the blood circulation system of a patient, and normally referred to as vascular access catheters. More particularly, the invention relates to such catheters having a connection structure at the proximal end for controlling flow of liquids through the catheter.

Vascular access catheters have been developed as single lumen, dual lumen or multi-lumen catheters and are used for a variety of procedures, all of which involve intrusion into the blood circulatory system. The main body of the catheter is designed for this intrusion and the proximal or outer end includes extensions, one for each lumen. It is common practice to make these extensions from flexible tubing so that they can be manipulated outside the body and held in any convenient position using surgical dressings. Each of the tubes normally carries a luer lock connector at its free end for attachment to fluid lines and for subsequent closing and sealing of the lumens when the catheter is not in use. Because these connectors may fail, it is also common practice to place a clamp on each of the extensions so that this can be used to close the extension by deforming it and to act as a second closure.

This second line of defence is made necessary because it is possible that the luer lock and its cap may fail due to misuse or to simple flaws created during manufacture. It is evident that should the lines of defence fail while the catheter is in place, the patient is at risk of bleeding to death or suffering an 'air embolism if the failure is not detected very quickly.

Flexible tubes and clamps are not extirely satisfactory. The most serious problem is that the clamps close the tubes by a pinching action and if the clamp is in place for a significant length of time, it is not uncommon that the tubing will not recover when the clamp is released. The resulting crease in the tubing causes flow problems and in extreme cases the catheter has to be removed because the tube is no longer patent. The problem is most prevalent on catheters that have thermoplastic tubular extensions made from polyvinylcholoride (PVC) or polyurethane (PU). Also the problem is exacerbated by the fact that these plastics are attacked in a mild way by organic solvents such as alcohol that is always present in heparin. This is an anti-coagulant drug that is used in the catheters when they are left in place in the patient in order to maintain the patency of the catheter for future use.

An alternative to PVC and PU is silicone rubber which is not attacked by solvents such as alcohol. Consequently the walls will not stick to one another, and this combined with the good rebound properties, make it suitable for use as extension tubes and some manufacturers use silicone rubber extensions for this reason. However there is a secondary problem which has resulted in silicone rubber being superseded by PVC or PU. This problem relates to the fact that silicone is not thermoplastic and does not bond readily. Consequently if silicone rubber is to be used the tubes must be engaged using a friction fit alone and of course such a fit is subject to disconnection and adds another risk factor to the use of the catheter. It is therefore most common to use PVC or PU extensions which are permanently bonded to the remainder of the catheter.

There are other problems associated with the use of clamps. It has been found that unless they are aligned accurately before they are engaged they can disengage by a minor impact. Also, clamps tend to have sharp edges which are required to crease the tube and these edges can result in cutting and shearing, particularly when silicone rubber tubing is used.

Accordingly vascular access catheters should include a structure for opening and closing the flow through the catheter which is reliable, maintains patency regardless of the time during which the catheter is not in use, and which does not have any connections which are a friction fit.

In one of its aspects the invention provides a dual lumen vascular access catheter having a main body defining first and second lumens and a connection structure channels extend from the respective first and second lumens for attaching the catheter to equipment, and first and second rotary valves are positioned in the respective first and second channels. The valves include operators rotatable in generally the same plane to operate the valves and to provide a ready visual indication of the positions of the valves.

This and other aspects of the invention will be better understood with reference to the drawings, in which:

FIG. 1 is an isometric view of a catheter incorporating a first embodiment of the invention and having independent rotary valves in a proximal end structure;

FIG. 2 is a sectional view of line 2—2 of FIG. 1;

Figure 5:
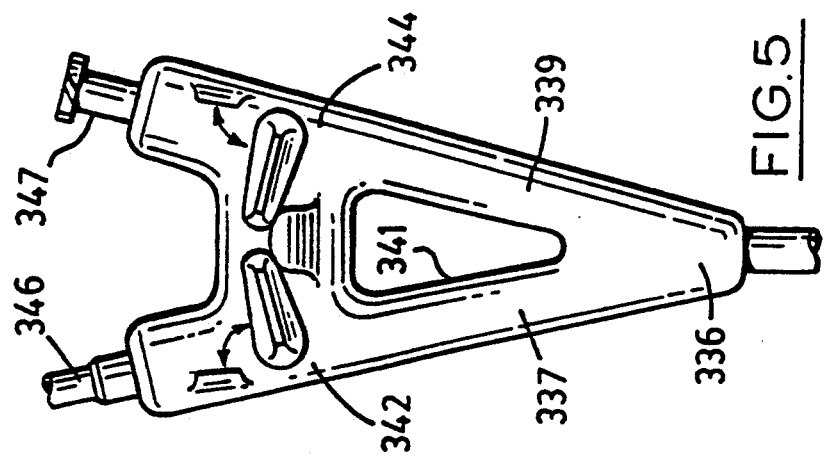
FIG. 5 is a view similar to FIGS. 3 and 4 and showing a fourth embodiment of proximal end structure.

Reference is made first to FIG. 1 which illustrates a dual lumen vascular access catheter designated generally by the numeral 20 and including a main body 22 having a tip 24 at and adjacent a distal end 26. The main body 22 terminates at a proximal end 28 adjacent a conventional suture wing structure 30 rotatably mounted on the main body 22 and retained in place by a collar 32 and by an end of proximal connection structure designated generally by the numeral 34. This connection structure consists of a lumen connector 36, intermediate flexible tubes 38, 40 which lead to respective rotary valves 42, 44 and which in turn lead to tubes 46, 48 attached to respective luer connectors 50, 52.

The lumen connector 36 forms the transition between the dual lumens in the main body 22 and the intermediate flexible tubes 38, 40. The main body could have the lumens in a side-by-side arrangement or be coaxial. In both instances, the lumens are separated for continuous flow between the respective tubes 38, 40 and the independent lumens. One lumen will project to the distal end 26 and is normally the return lumen and the other lumen is the intake lumen and will originate at openings 54 providing entry to the catheter. Flow will proceed through the lumen connector 36 and then by way of tube 40 and other parts. The return flow is through the luer connector 50 and passes eventually through the lumen connector 36 on its way to the distal end 26 and associated openings 56.

The rotary valves 42, 44 are identical in structure but could be colour coded as is conventional to show intake and outlet lumens. As better seen in FIG. 2, the rotary valve 42 includes a housing 58 defining a conical opening 60 which contains a conical shaft 62. This shaft has an extension 64 on which is mounted a spring washer 66 and a flat washer 68. The flat washer is a friction fit on the extension 64 and the spring washer biases the shaft 62 into the opening 60 to seal these two parts one against the other. The washers are contained in a cavity 70 which is conveniently sealed by a thin disk 72 which is a snap fit in a groove in the cavity.

At its upper extremity the shaft 62 has a transverse bar 74 attached to the shaft and providing a small clearance with the housing 58 so that the bar does not interfere with the biasing forces created by the spring washer 66 to seat the shaft in the opening 60. The bar 74 permits the user to rotate the bar and the shaft which brings an opening 76 in the shaft 62 into alignment with a similar opening 78 in the housing 58. The opening 78 forms part of a continuous channel 79 extending from the main body (FIG. 1) to the luer connected 52. The channel is connected in the lumen connector 36 to an appropriate one of the lumens in the main body 22 as previously mentioned a similar channel exists in tube 40 and associated parts.

As seen in FIG. 1 the bar 74 is in alignment with the channel 79 (FIG. 2) formed in the structure and closes the channel. The bar can be rotated as indicated in ghost outline with reference to the rotary valve 44 to bring the openings 76 and 78 (FIG. 2) into alignment for continuity of the channel. This permits opening and closing of the channel as required for flow through the catheter.

The materials used in manufacturing the connection structure 34 are compatible for bonding one to another either by the direct use of heat or by the use of solvents. Suitable materials would include polyvinylchloride (PVC) or polycarbonate.

The structure shown in FIG. 1 has advantages in particular types of use where some flexibility is required. It is common to use a femoral, jugular, or subclavian intrusions and because of the requirements of the patient, different methods of attachment and different forms of catheters will be appropriate. In the structure shown in FIG. 1 the front flexibility provided in the intermediate flexible tubes 38, 40 will permit the catheter to be taped in position with the limitation that the connection structure 34 extends generally in the direction of the main body 22. Consequently it must be attached by first suturing the structure to the patient using the wing structure 30, and then tapes and dressings would be used to attach some of the remaining structure to the patient leaving the bar 74 and its equivalent 80 available for use. One of the advantages of the structure shown in FIG. 1 is that the flexibility in the tubes 38, 40 will permit the valves to be attached independently.

Figure 3:
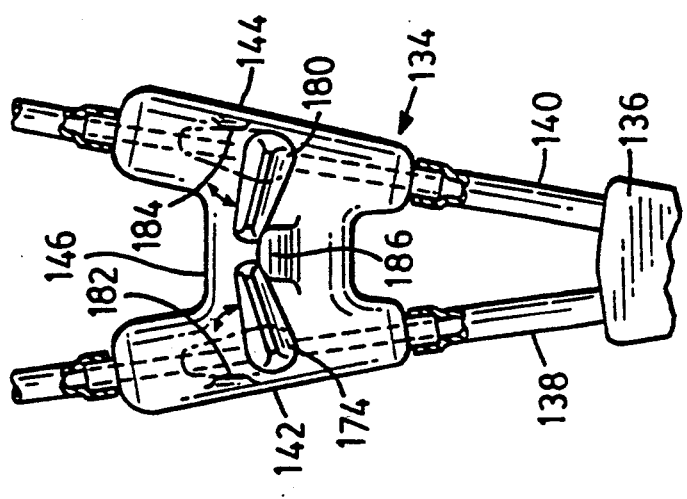
FIG. 3 is a side view of part of a proximal end structure of a second embodiment.

In some situations it will be more secure to have the connection structure 34 arranged with a connection between the valves. Such an arrangement is shown in FIG. 3. In this arrangement a lumen connector 136 is attached to flexible tubes 138,140 and a pair of rotary valves 142,144 are connected to one another by a bridge 146. In this instance levers 174, 180 are used to operate the valves and they are arranged so that in the position shown in FIG. 3, the channels through the connection 134 are closed. Rotation of the levers (indicated by the arrows) will bring them into general alignment with the channels in which case the channels are opened. The positions for the levers are defined by respective raised stops 182,184 and a central stop 186.

In the structure shown in FIG. 3, the flexibility in the tubes 138, 140 will permit the structure to be put in position and attached to the patient taking into consideration some curvature in the patient's body in the area immediately adjacent the intrusion site. The diverging angle between the tubes 138,140 is continuous with the channels in the connection structure. This is advantageous because the luer connectors are then separated to make it easier for manual connection. The angle of divergence is generally about 15° but is preferably less than 30° to minimize extreme diversion and separation of the luer connectors.

Figure 4:
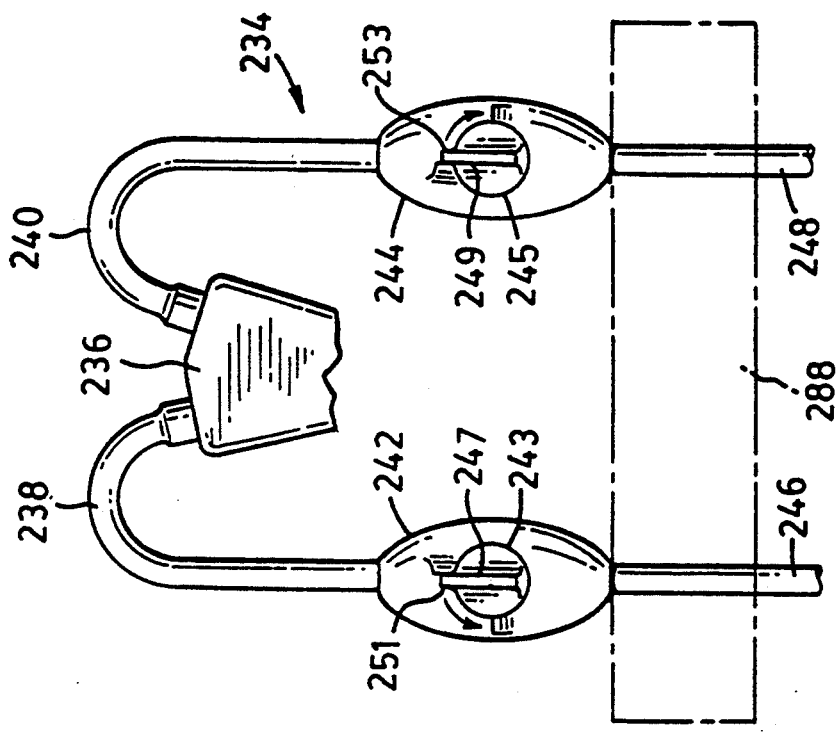
FIG. 4 is a view similar to FIG. 3 and showing a third embodiment of proximal end structure.

Reference is next made to FIG. 4 which illustrates a third embodiment of connection structure indicated generally by the numeral 234. This is particularly advantageous in sites where there is a difficulty with attachment to locations in general alignment with the main body of the catheter. Such instances would arise in jugular intrusions. Here a pair of flexible tubes 238 and 240 are provided leading from a lumen connector 236 and the tubes 238,240 are precurved into a general U-shaped configuration. Consequently the tubes lead from the lumen connector 236 and then extend in generally parallel arrangement meeting the rotary valves 242 and 244 which in turn lead to tubes 246 and 248. A suitable dressing is indicated at 288 in ghost outline. This would be used in association with the wing structure 30 shown in FIG. 1.

As seen in FIG. 4, the rotary valves 242,244 are operated by respective round knobs 243,245 which include raised bars 247,249 for easier grip. Associated with the knobs are short extensions 251 and 253 for engagement with raised stops to locate the valve in open or closed positions in a similar manner as that shown in FIG. 3. Here again, the bars 247,249 are shown in an open position in alignment with the channels as is conventional in rotary valves.

A further embodiment is shown in FIG. 5. This fourth embodiment is a unitary structure which dispenses with the use of flexible tubes such as 38 and 40 shown in FIG. 1. Here there is a portion forming an integral lumen connector 336 which extends to a pair of diverging channel sections 337,339 which separate about an opening 341 provided simply to lighten the structure. These sections meet rotary valves 342,344 formed in the unitary structure and having lever arrangements such as those shown in FIG. 3.

Two forms of connections are shown in FIG. 5, the first being a simple tube 346 which corresponds to that previously described, and the other being an integral luer connector 347.

The structure shown in FIG. 5 would be used where the access site permits the unitary structure to be tied down to the patient conveniently without stress being transferred to the portion of the catheter inserted in the patient.

Figure 6:
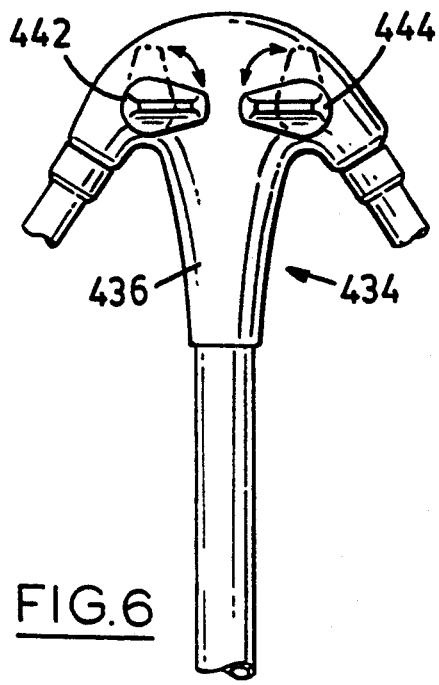
FIG. 6 is a view similar to FIGS. 3, 4 and 5 and showing a fifth embodiment of proximal end structure.
Figure 7:
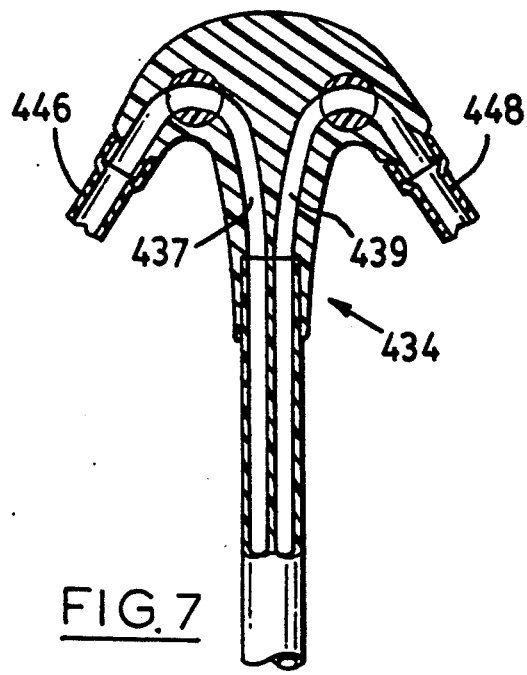
FIG. 7 is a sectional view of the structure shown in FIG. 6 to illustrate internal structure.

Another form of unitary connection structure is indicated at 434 in FIGS. 6 and 7. Here the connection structure 434 includes an integral lumen connector 436 leading to curved channels 437 and 439 which pass rotary valves 442 and 444. The curved channels terminate at tubular extensions 446,448 but could of course be arranged with luer connectors such as 347 shown in FIG. 5. The rotary valves are equipped with levers in the fashion of those shown in FIGS. 3 and 5, and the diverging tubes 446,448 can be arranged with any angle depending upon the molding shape selected. This arrangement has particular advantage where it is necessary to bring the tubes 446,448 more or less back in the direction of the main body.

Figure 8:
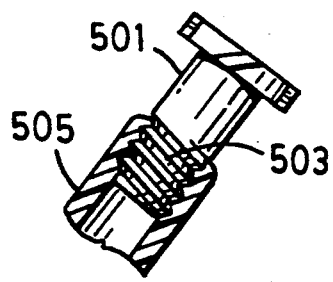
FIG. 8 is a sectional view of a portion of an embodiment illustrating a screw-in luer connector usable in all of the embodiments.

FIG. 8 is a sectional view of a form of luer connector which can be used with this structure. Instead of having fixed luer connectors, the connector 501 has a left-handed thread 503 for engagement in a housing 505 forming part of a connection structure. Consequently if the luer connector should be defective in any way, it can be removed by threading it out of the connection structure and replacing it with another luer connector. This helps to enhance the efficiency of the catheter because it is no longer necessary to remove the whole catheter in order to replace the luer connector.

A series of different embodiments have been shown which are preferred in different circumstances. They all include a connection structure at the proximal end of the main body and operate in similar fashions to one another. All have rotary valves and operators such as bars which provide a ready visual indication of the positions of the valves.

In some instances, it will be important to use a catheter which has a minimum of external structure. Embodiments such as those shown in FIGS. 5 and 6 lend their design to creating small structures simply by bringing the parts as close as possible to the main body and minimizing the dimensions. This capability is a further advantage of the invention.

It will be evident that a great variety of embodiments are possible within the limitations of the invention as claimed and all such embodiments are incorporated in this invention.

We claim:

1. A dual lumen vascular access catheter comprising:
   a main body defining first and second lumens and extending longitudinally between proximal and distal ends, the first lumen terminating at the distal end and the second lumen being shorter than the first lumen and terminating at a point spaced from the distal end;
   connection structure having coupling means attaching the structure to the main body at the proximal end, first and second channels for attaching the catheter to dialysis equipment, the channels extending from the respective first and second lumens, first and second rotary valves positioned in the respective first and second channels and operable for selectively opening and closing the channels as required during and between dialysis treatments and;
   each of the rotary valves including an operator moveable angularly about an axis to open and close the valves, the operators being moveable generally in the same plane with the axes generally parallel, whereby in use, the catheter can be arranged with the operators exposed for ready visual identification of the positions of the operators and thereby the positions of the rotary valves.

2. A dual lumen catheter as claimed in claim 1 in which each of the channels includes a section of flexible tubing.

3. A dual lumen catheter as claimed in claim 2 in which the sections of flexible tubing are generally U-shaped.

4. A dual lumen catheter as claimed in claim 1 in which each of the channels is curved.

5. A dual lumen catheter as claimed in claim 3 in which the generally U-shaped sections of tubing naturally lie in a common plane when not in use and curve away from one another as they extend away from the main body.

6. A dual lumen catheter as claimed in claim 4 in which the channels curve away from one another as they extend away from the main body.

7. A dual lumen catheter as claimed in claim 6 in which the channels lie in a common plane.

* * * * *